United States Patent [19]
Griffiths

[11] Patent Number: 5,914,047
[45] Date of Patent: Jun. 22, 1999

[54] ON-SITE BIOHAZARDOUS LIQUID MEDICAL WASTE COLLECTION AND TREATMENT SYSTEM AND METHOD OF USING SUCH SYSTEM

[75] Inventor: Gerald R. Griffiths, Belguim, Wis.

[73] Assignee: Grifco, LLC, Belgium, Wis.

[21] Appl. No.: 08/885,549

[22] Filed: Jun. 30, 1997

[51] Int. Cl.⁶ .............................. B01D 17/12; A61L 2/24; B01F 5/06
[52] U.S. Cl. ..................... 210/739; 210/101; 210/139; 210/198.1; 210/764; 366/337; 366/341; 422/40; 422/106; 422/116; 604/319; 604/320; 604/322
[58] Field of Search ................................. 210/101, 103, 210/104, 139, 198.1, 205, 206, 257.1, 739, 741, 744, 745, 764, 808, 94; 422/28, 40, 41, 105, 106, 112, 116, 119, 33; 604/317–320, 322, 323, 324, 326; 366/337–341

[56] References Cited

U.S. PATENT DOCUMENTS

| | | |
|---|---|---|
| 3,591,493 | 7/1971 | Zeineh . |
| 4,384,580 | 5/1983 | Leviton ................................... 604/319 |
| 4,465,485 | 8/1984 | Kashmer et al. ....................... 604/320 |
| 4,475,904 | 10/1984 | Wang ....................................... 604/119 |
| 4,643,197 | 2/1987 | Greene et al. .......................... 604/319 |
| 4,795,448 | 1/1989 | Stacey et al. ........................... 604/319 |
| 4,870,975 | 10/1989 | Cronk et al. ............................ 604/317 |
| 5,092,858 | 3/1992 | Benson et al. .......................... 604/319 |
| 5,093,058 | 3/1992 | Harmon et al. ......................... 366/337 |
| 5,145,256 | 9/1992 | Wiemers et al. ........................ 366/337 |
| 5,185,007 | 2/1993 | Middaugh et al. ..................... 604/320 |
| 5,234,419 | 8/1993 | Bryant et al. ........................... 604/320 |
| 5,242,434 | 9/1993 | Terry ........................................ 604/317 |
| 5,349,722 | 9/1994 | Chayer ...................................... 15/353 |
| 5,419,259 | 5/1995 | Naficy ..................................... 210/764 |
| 5,516,423 | 5/1996 | Conoby et al. ......................... 210/96.1 |
| 5,605,400 | 2/1997 | Kejima .................................... 366/341 |
| 5,741,237 | 4/1998 | Walker .................................... 604/322 |
| 5,741,238 | 4/1998 | Bradbury et al. ...................... 604/322 |
| 5,776,118 | 7/1998 | Seifert et al. ........................... 604/317 |

FOREIGN PATENT DOCUMENTS

0 184 629   6/1986   European Pat. Off. .
WO 96/26750   9/1996   WIPO .

OTHER PUBLICATIONS

Introducing SafeCycle 40 Hands–Off Fluid Waste Management, Steris Corporation, undated.

*Primary Examiner*—Joseph W. Drodge
*Attorney, Agent, or Firm*—Andrus, Sceales, Starke & Sawall

[57] ABSTRACT

A biohazardous liquid medical waste collection and treatment system provides on-site collection and treatment of surgical fluids. The system is mobile, and includes an upper unit and one or more lower units that are detachable from the upper unit. The upper unit includes a liquid disinfectant reservoir, liquid pump valves, and an electronic control unit which controls the operation of the pump valves. A disposable suction canister is mounted to the upper unit and collects liquid medical waste aspirated from a patient. A disposable tube set, including a motionless mixer, is connected to the disposable suction canister and the liquid disinfectant reservoir. Electronically controlled pumps (preferably peristaltic pumps) pump liquid waste from the suction canister along with the metered amount of liquid disinfectant from the liquid disinfectant reservoir through the motionless mixer and into a temporary storage receptacle on the lower unit. When full, the lower unit is detached from the upper unit and a battery powered discharge pump empties the lower unit. A timer relay is provided on the lower unit to postpone discharge pump operation until the expiration of a preselected disinfectant treatment time.

55 Claims, 6 Drawing Sheets

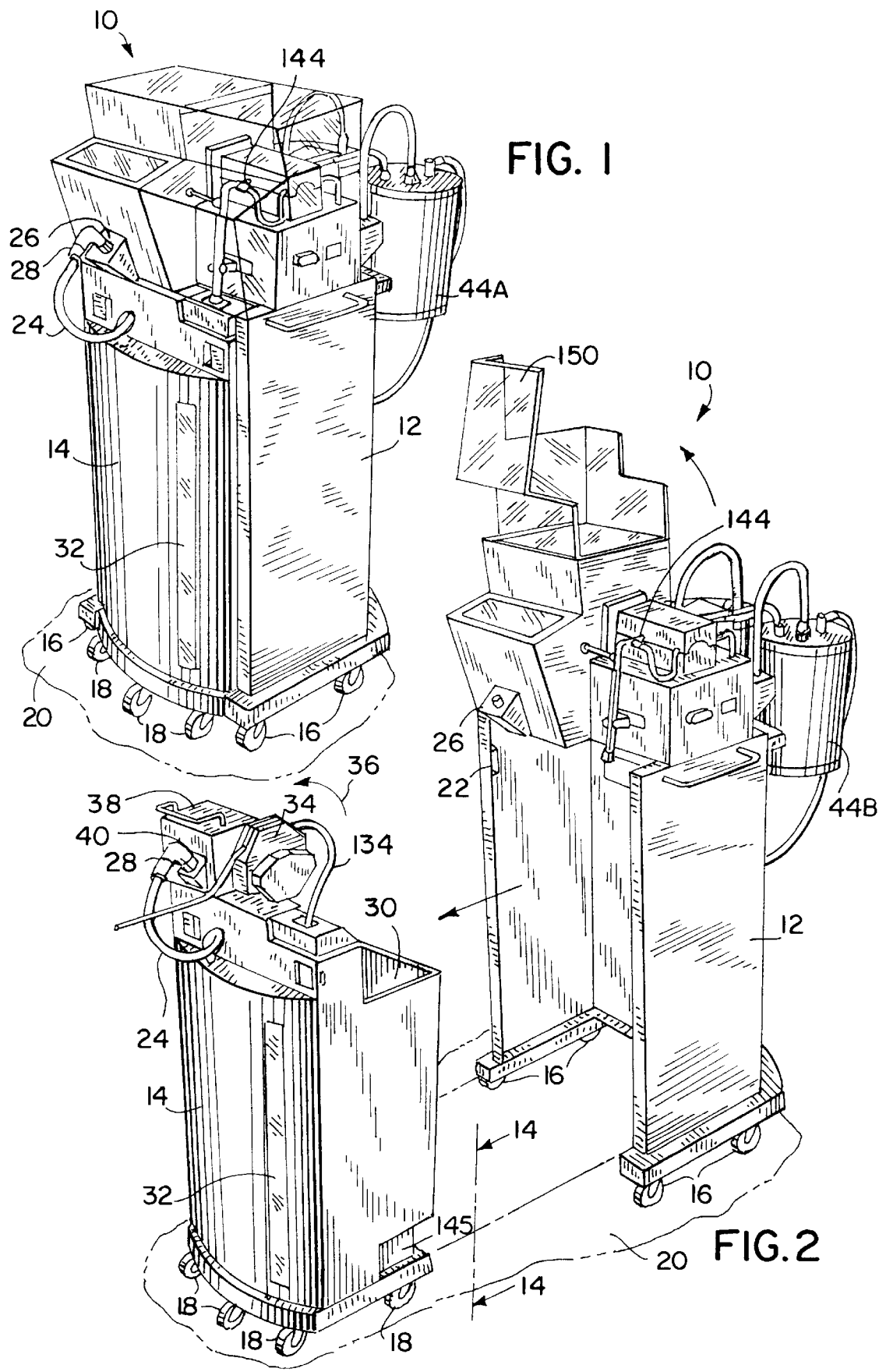

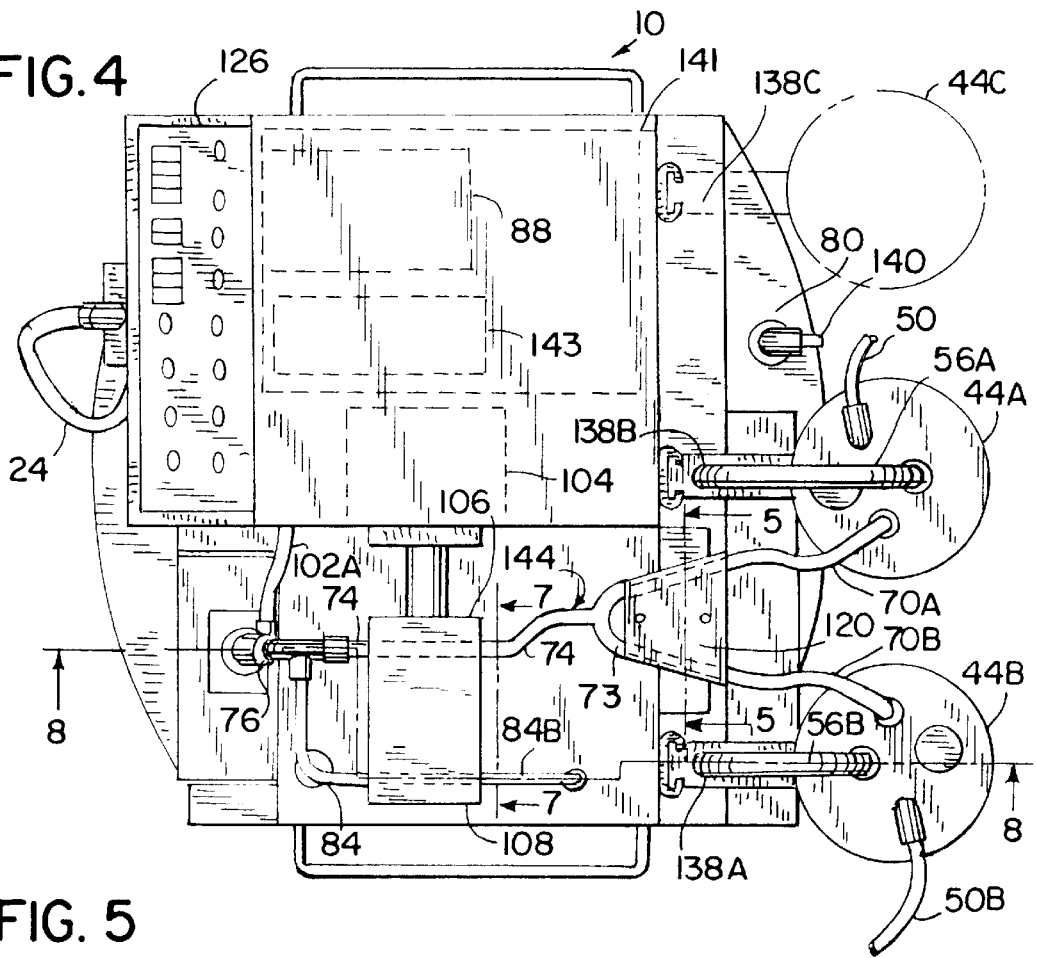
FIG. 4
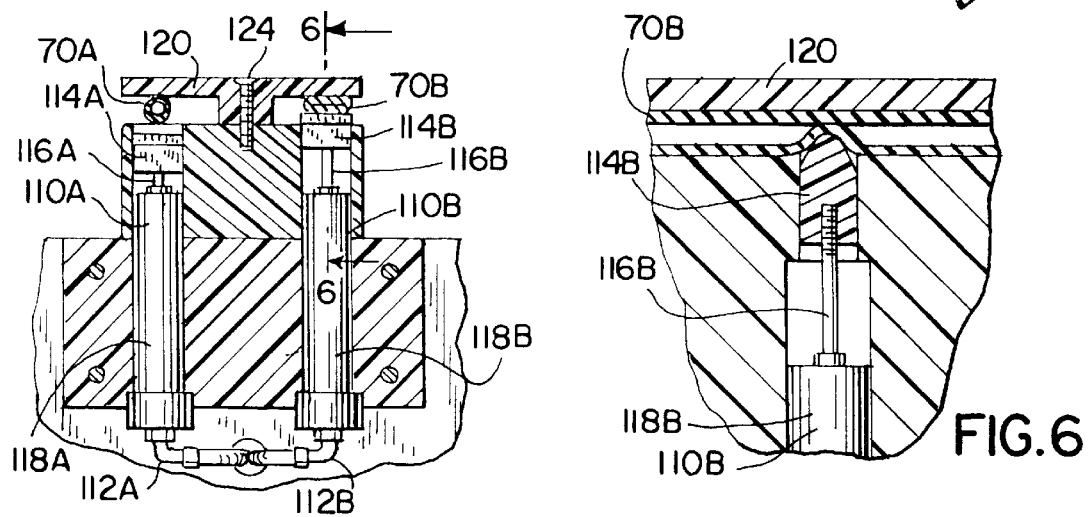
FIG. 5
FIG. 6
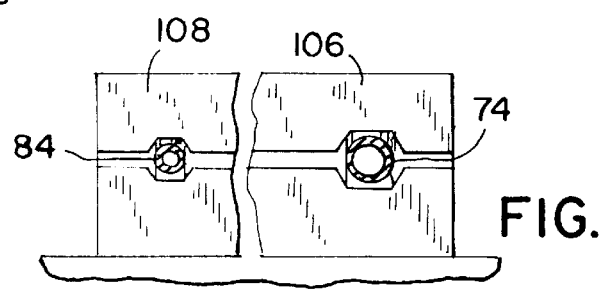
FIG. 7

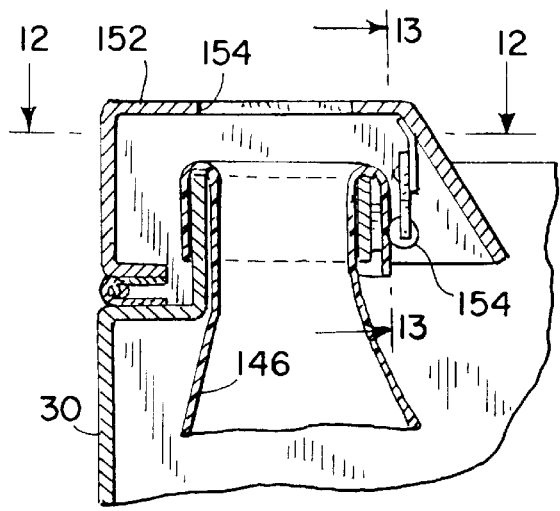
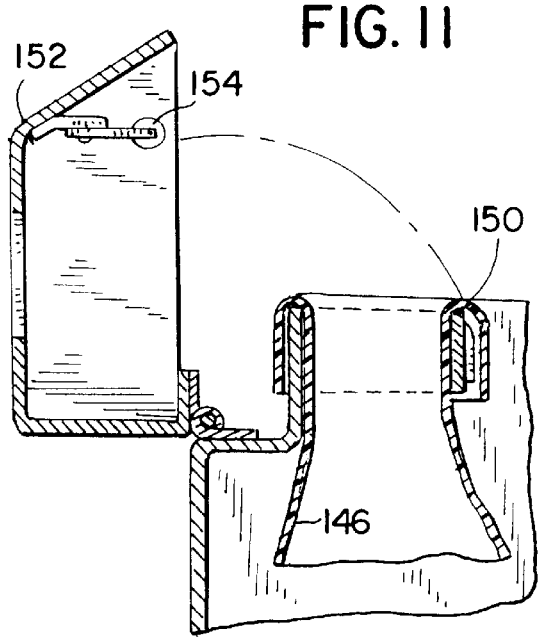
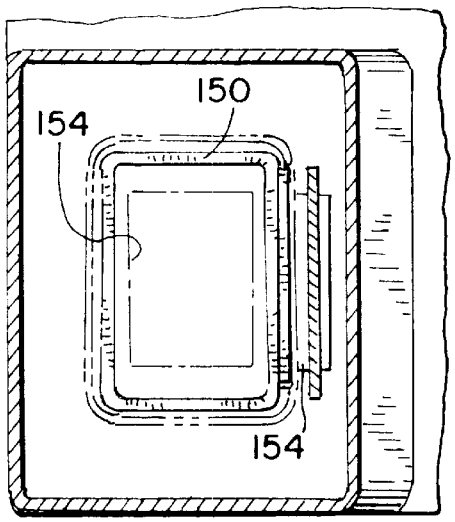
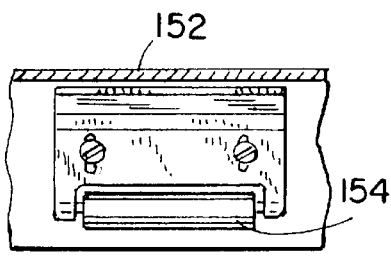
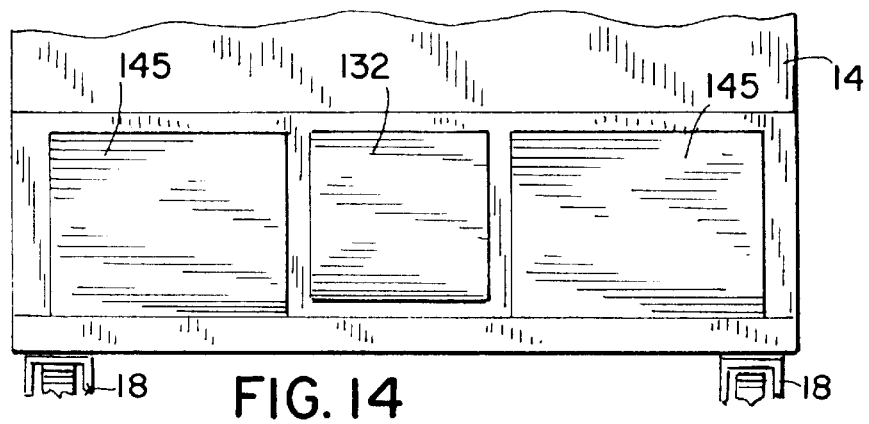

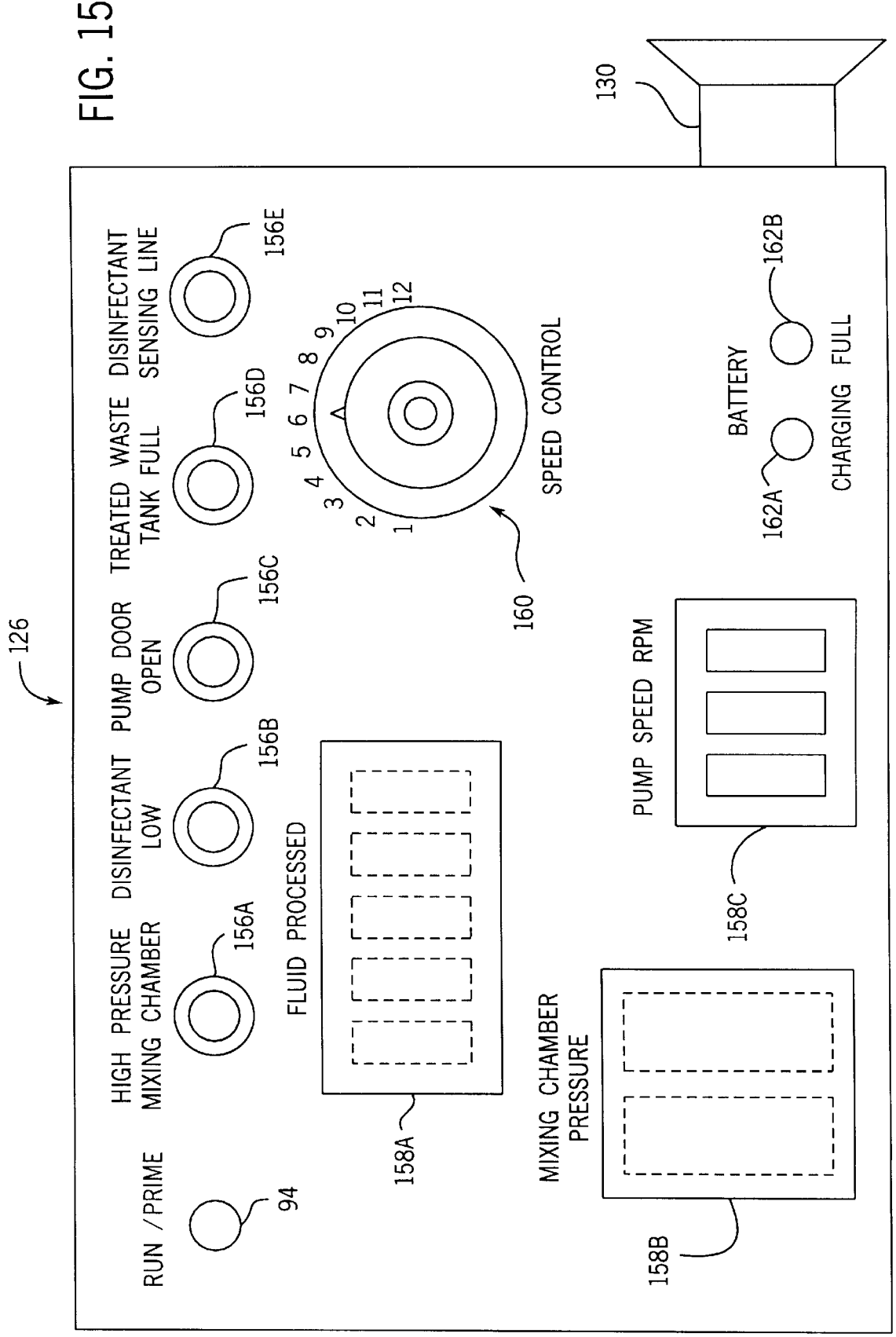

ON-SITE BIOHAZARDOUS LIQUID MEDICAL WASTE COLLECTION AND TREATMENT SYSTEM AND METHOD OF USING SUCH SYSTEM

FIELD OF THE INVENTION

The invention relates to the collection and treatment of biohazardous liquid medical waste, for example, from patients during surgical procedures. In particular, the invention is a system and method for treating biohazardous liquid medical waste on-site immediately after collection.

BACKGROUND OF THE INVENTION

Suction drainage systems are often used during surgical procedures to drain body fluids from a patient. Most hospitals use suction drainage systems that employ one or more disposable suction canisters connected to a vacuum source to create a vacuum within the interior of the disposable canister. A flexible suction tube extends from the disposable canister to the source of body fluids in the patient. The vacuum within the canister draws the body fluids through the suction tube into an internal liquid waste receptacle within the canister. These surgical fluids are considered to be biohazardous waste, mostly because of the risk of infection upon exposure.

In many surgical procedures, the volume of body fluids collected in the suction canister exceeds the capacity of a single disposable suction canister. For instance, arthroscopic surgery procedures using saline as a medium generate large volumes of surgical fluids. It is not uncommon to use 20–30 liters of saline during an arthroscopic knee surgery. It is generally accepted that these large volumes of surgical fluids should be regulated and treated as a biohazardous liquid waste.

Usually, it is desirable to collect fluids continuously from the patient without having to interrupt suction when a first suction canister becomes full. To prevent interruptions, two or more suction canisters are typically connected in a serial collection arrangement to accommodate large volumes of surgical fluid. See, for instance, U.S. Pat. No. 4,384,580, entitled "Suction Canister System and Adaptor for Serial Collection of Fluids", by Jan Leviton, assigned to Beckton Dickinson Co., issued on May 24, 1983. Canister racks are used to hold the series of disposable canisters. It is not uncommon to use as many as 20 or even 30 disposable suction canisters during a single surgery.

The handling and disposal of surgical fluids in disposable suction canisters creates a risk of infection to health care workers handling the canisters, especially if the fluids spill or splash. Thus, it is important to keep untreated liquid medical waste isolated, at least until it has been treated properly with a disinfectant (e.g. thorough mixing of liquid medical waste with a chlorine-based disinfectant for an appropriate time period sufficient to rid infectious bacteria and the like). By its nature, liquid medical waste is heavy. Therefore, if the liquid waste is not treated on-site, the cost of shipping the liquid medical waste and disposing the liquid waste at a remote waste treatment center can be financially burdensome. Perhaps due to disposal costs and perhaps due to convenience, there is a tremendous temptation for health care workers to dispose of the untreated liquid medical waste by simply dumping untreated waste into the hospital drain system. Some states and local municipalities restrict this practice, while others do not. Nonetheless, the likelihood of exposure and infection to a health care worker is increased greatly if the health care worker handles and disposes untreated medical waste in this manner.

Several prior art patents disclose techniques designed to facilitate the handling and disposal of biohazardous liquid medical waste. For instance, U.S. Pat. No. 5,185,007 entitled "Suction Drainage and Infection Control System" by Migdow, et al., assigned to Abbott Laboratories, issued on Feb. 9, 1993 and U.S. Pat. No. 5,234,491 entitled "Suction Drainage Infection Control System" to Bryant et al. and assigned to Abbott Laboratories, issued Aug. 10, 1993 describe various techniques for releasing disinfectant into a disposable suction canister to treat the liquid medical waste on-site. One problem with these systems is that the disinfectant is often not thoroughly mixed with the liquid waste. This is especially important when clotted blood is present in the liquid waste because thorough mixing is needed so that the treatment chemical can effectively permeate the blood clots and deactivate infectious organisms.

U.S. Pat. No. 4,900,500 discloses a solidifying agent or gelling compound that is added to the liquid waste after the disposable canister is full, thereby reducing the likelihood of spilling from the disposable canister. After the liquid waste has been solidified, the disposable canister filled with gelled liquid waste is disposed at an incinerator, a landfill or the like. One problem with this technique is that the health care worker must physically open a contaminated canister to add the gelling compound, thus taking the risk of spilling or splashing infectious liquid medical waste as well as exposing the worker to airborne contaminants. To avoid this problem, it is desirable to add disinfectant before solidifying the liquid medical waste in the canister. U.S. Pat. No. 5,092,858 discloses a system designed to solve the problem of inadequate mixing between infectious liquid medical waste and disinfectant due to premature solidification of the liquid medical waste.

The Steris Corporation, Mentor, Ohio (U.S. Pat. No. 5,242,434 entitled "Medical Waste Handling System", by Terry, issued on Sep. 7, 1993) has provided a fluid waste management system that completely replaces the use of disposable suction canisters, and has the ability to treat biohazardous liquid medical waste internally on-site. However, this system has several limitations which compromise its effectiveness. The system contains two concealed, non-disposable canisters having a total capacity of about 40 liters. The canisters are concealed within a metal housing. Liquid disinfectant is put into the concealed canisters before system start-up to disinfect suction drainage fluids collected in the canisters. Surgeons cannot visually monitor the quality of the suction drainage fluid because the canisters are concealed. When the canisters are filled or the surgery is complete, the system must be taken offline for draining and cleaning if it is desired to use the system on another patient.

SUMMARY OF THE INVENTION

The invention is an on-site liquid waste collection and treatment system that eliminates the need of using large numbers of disposable suction canisters, yet can be used continuously with unlimited capacity. In addition, the system ensures that liquid disinfectant is properly metered, thoroughly mixed and held for a sufficient period of time with the liquid waste to effectively kill infectious organisms. The treated liquid waste can then be safely disposed on-site without risking infection.

In the preferred embodiment, the invention is a mobile, on-site biohazardous liquid medical waste collection and treatment station comprising an upper unit and a lower unit that is detachable from the upper unit. The upper unit includes a suction chamber, preferably detachable and disposable, identical or similar to disposable suction canisters which are known in the art. A suction tube, preferably disposable, is connected to a liquid intake port on each suction chamber also as known in the art. The upper unit includes a vacuum port that is connected to a vacuum source when the station is operating. A vacuum is created in the one or more suction chambers to draw liquid waste through the suction tube into an internal liquid waste reservoir in the respective suction chamber. The upper unit also includes a liquid disinfectant reservoir. When a sufficient amount of liquid waste is present in the internal receptacle of the respective suction chamber, a liquid waste pump displaces the liquid waste from the internal liquid waste receptacle of the suction chamber to a waste treatment mixer. Contemporaneously, a liquid disinfectant pump displaces liquid disinfectant from the liquid disinfectant reservoir to the waste treatment mixer. Alternatively, liquid disinfectant can be provided to the waste treatment mixer by a gravity feed. The waste treatment mixer is preferably a motionless mixer that thoroughly mixes the liquid waste and the liquid disinfectant. The mixture of liquid waste and liquid disinfectant dumps into a treated waste temporary storage receptacle that is located within the lower unit.

When the treated waste temporary storage receptacle in the lower unit becomes full, the lower unit can be detached from the station and moved away, while another identical or similar lower unit can be moved in to replace the first lower unit. A plurality of wheels are mounted to the lower unit which enables the lower unit to be easily rolled over a floor. Normally, the amount of time to replace the lower unit is much less than the amount of time it takes to fill one of the suction chambers. Therefore, a biohazardous liquid waste collection and treatment station in accordance with the invention, can immediately treat and process virtually an unlimited amount of surgical fluid continuously without interruption.

The lower unit includes a sight tube that enables visual monitoring of the liquid waste collected in the treated waste temporary storage receptacle. This is helpful not only to gauge the amount of liquid in the lower unit, but also allows the surgeon or other health care workers to monitor the consistency of the liquid waste, (e.g., visual monitoring of the amount of blood collected from the patient during a surgical procedure). In addition, the one or more suction chambers are preferably mounted to the upper unit in a location that is easily monitored by visual inspection.

The lower unit includes a treated waste discharge pump that discharges the mixture of liquid waste and liquid disinfectant from the treated waste temporary storage receptacle in the lower unit into a remote drain or the like for disposal. For most disinfectants, it is important that the mixture of liquid waste and liquid disinfectant remain isolated for a certain time period to enable full effectiveness of the liquid disinfectant and render the mixture aseptic. Thus, the lower unit includes a timer relay that postpones operation of the treated waste discharge pump until a sufficient time has passed since a fresh mixture of liquid waste and liquid disinfectant poured into the treated waste temporary storage receptacle in the lower unit. In this manner, pumping the mixture out of the lower unit can occur only after the mixture has been held in the lower unit beyond expiration of the required time period for the disinfectant to be effective.

The lower unit preferably includes a splashguard that is used to support the top end of a disposable plastic liner within the liquid waste temporary storage receptacle. The treated waste discharge pump is preferably a peristaltic pump that pumps treated liquid waste from the receptacle in the lower unit through a discharge hose passing into the disposable plastic liner through the splashguard. The size of the splashguard is relatively small compared to the size of the treated waste temporary storage receptacle in the lower unit, therefore requiring the disposable plastic liner to neck together at the splashguard. A cover having a small access opening encloses the treated waste temporary storage receptacle in the lower unit, thus providing access to treated liquid waste in the receptacle in the lower unit through the splashguard with the discharge hose or the like.

While the upper unit preferably has an AC electrical power receptacle so that the upper unit can receive AC electrical power from a conventional electrical power outlet (110 volts AC), the treated waste discharge pump on the lower unit preferably operates on DC power provided by a battery on the lower unit. This allows treated liquid waste collected in the lower unit to be discharged easily in a location remote from an AC electrical power receptacle. The upper unit preferably includes a battery charger that charges the battery on the lower unit when the lower unit is attached to the upper unit.

It is preferred that the liquid waste pump and the liquid disinfectant pump on the upper unit be peristaltic pumps, although the invention is not necessarily limited to the use of peristaltic pumps. Peristaltic pumps are especially well suited for this application because peristaltic pumps are reliable, and by using peristaltic pumps there is no need to clean the pumps between patients. When using a peristaltic liquid waste pump and a peristaltic disinfectant pump, it is preferred to use an integral disposable tube set for each patient. The preferred tube set includes a main tube portion in which a motionless mixer is installed. The tube set also includes an untreated liquid waste tube portion for each of the one or more suction chambers. Each untreated liquid waste tube portion leads into the main tube portion and has a quick connect inlet which connects to the respective suction chamber. The tube set also includes a liquid disinfectant tube portion that leads into the main tube portion and has a quick connect inlet which connects to the liquid disinfectant reservoir on the upper unit. The liquid disinfectant tube portion preferably enters the main tube portion at a location downstream of the location that the one or more untreated liquid waste tube portions enter the main tube portion. The liquid waste peristaltic pump displaces liquid waste through the main tube portion upstream of the location where the liquid disinfectant tube portion leads into the main tube portion. The liquid disinfectant peristaltic pump displaces liquid disinfectant through the liquid disinfectant tube portion. Preferably, a common drive is used to drive both the liquid waste peristaltic pump and the liquid disinfectant peristaltic pump. The size of the main tube portion and the size of the liquid disinfectant tube portion are selected so that the amount of liquid disinfectant flowing through the liquid disinfectant tube portion is metered in proportion to the amount of liquid waste flowing through the main tube portion. In this manner, an appropriate amount of liquid disinfectant is mixed with the biohazardous liquid waste even when the speed of the liquid waste pump varies. The motionless mixer preferably includes a plurality of baffles or the like designed to thoroughly mix the liquid waste and liquid disinfectant passing through the tube set. Preferably, an integral pressure tap tube portion is connected to the main tube portion upstream of the motionless mixer. The pressure tap is used to monitor the pressure between the pumps and the mixer so that the pumps can be disabled in case excessive pressure is detected indicating that the mixer may be clogged.

In many circumstances, it is desirable to provide more than one active suction tube in a hospital operating room. The station therefore accommodates the use of a varying number of suction chambers. In particular, the station includes a valve system assigning a dedicated valve to each suction chamber. An untreated liquid waste tube portion of the tube set extends between each suction chamber into the main tube portion of the tube set. The dedicated valve opens the respective untreated liquid waste tube portion only when a sufficient level of liquid waste is present in the respective suction chamber.

There are several other features and advantages of the invention which will be apparent to those skilled in the art upon reviewing the following drawings and description thereof. For instance, there are several novel uses of sensors in the preferred embodiment of the invention. Many of the sensors are used to monitor system status and disable system operation under certain circumstances. One such example includes the use of a sensor to monitor the presence of liquid disinfectant in the liquid disinfectant tube downstream of the liquid disinfectant pump. System operation is disabled when no liquid disinfectant is present in the liquid disinfectant tube downstream of the liquid disinfectant pump.

From the foregoing description of the invention, it should be apparent to those skilled in the art that the system in accordance with the preferred embodiment of the invention instantly treats biohazardous liquid waste with liquid disinfectant, and is also fully enclosed to prevent spillage or any contact with health care workers until the liquid disinfectant has been thoroughly mixed with the liquid waste and the mixture has been held for a sufficient amount of time to render the treated liquid waste aseptic. In addition, the invention can be used to continuously collect and treat an unlimited amount of biohazardous liquid waste without requiring system shutdown for drainage or cleaning. Further, in the preferred embodiment of the invention, disposable suction chambers, as well as disposable tube sets, are used so clean up between cases is minimized. Nevertheless, the invention eliminates the need to connect large numbers of suction canisters in series to provide sufficient storage capacity, and also essentially eliminates the risk and cost of disposing of the liquid waste as regulated medical waste, without compromising convenience for health care workers.

BRIEF DESCRIPTION OF THE SEVERAL VIEWS OF THE DRAWINGS

FIG. 1 is a perspective view of a mobile station for collecting and treating biohazardous liquid medical waste on-site in accordance with a preferred embodiment of the invention;

FIG. 2 is a view similar to FIG. 1 showing a lower unit of the station detached from an upper unit of the station;

FIG. 4 is a top plan view of the biohazardous liquid waste collection and treatment station shown in FIG. 1;

FIG. 5 is a view taken along line 5—5 in FIG. 4 showing the operation of solenoid valves;

FIG. 6 is a sectional view taken along line 6—6 in FIG. 5;

FIG. 7 is a view taken along line 7—7 in FIG. 4 illustrating the relative sizes of tubing in the preferred embodiment of the invention;

FIG. 10 is a detailed view of a splashguard used in the lower unit to support a disposable plastic liner within a treated waste receptacle in the lower unit;

FIG. 11 is a view similar to FIG. 10 showing a cover for the lower unit in an open position;

FIG. 12 is a view taken along line 12—12 in FIG. 10;

FIG. 13 is a view taken along line 13—13 in FIG. 10; and

FIG. 14 is a view of a portion of the lower unit taken along line 14—14 in FIG. 2.

FIG. 15 is a schematic view of the preferred display panel for the biohazardous liquid waste collection and treatment system shown in FIGS. 1 and 2.

DETAILED DESCRIPTION OF THE DRAWINGS

Figure 3:
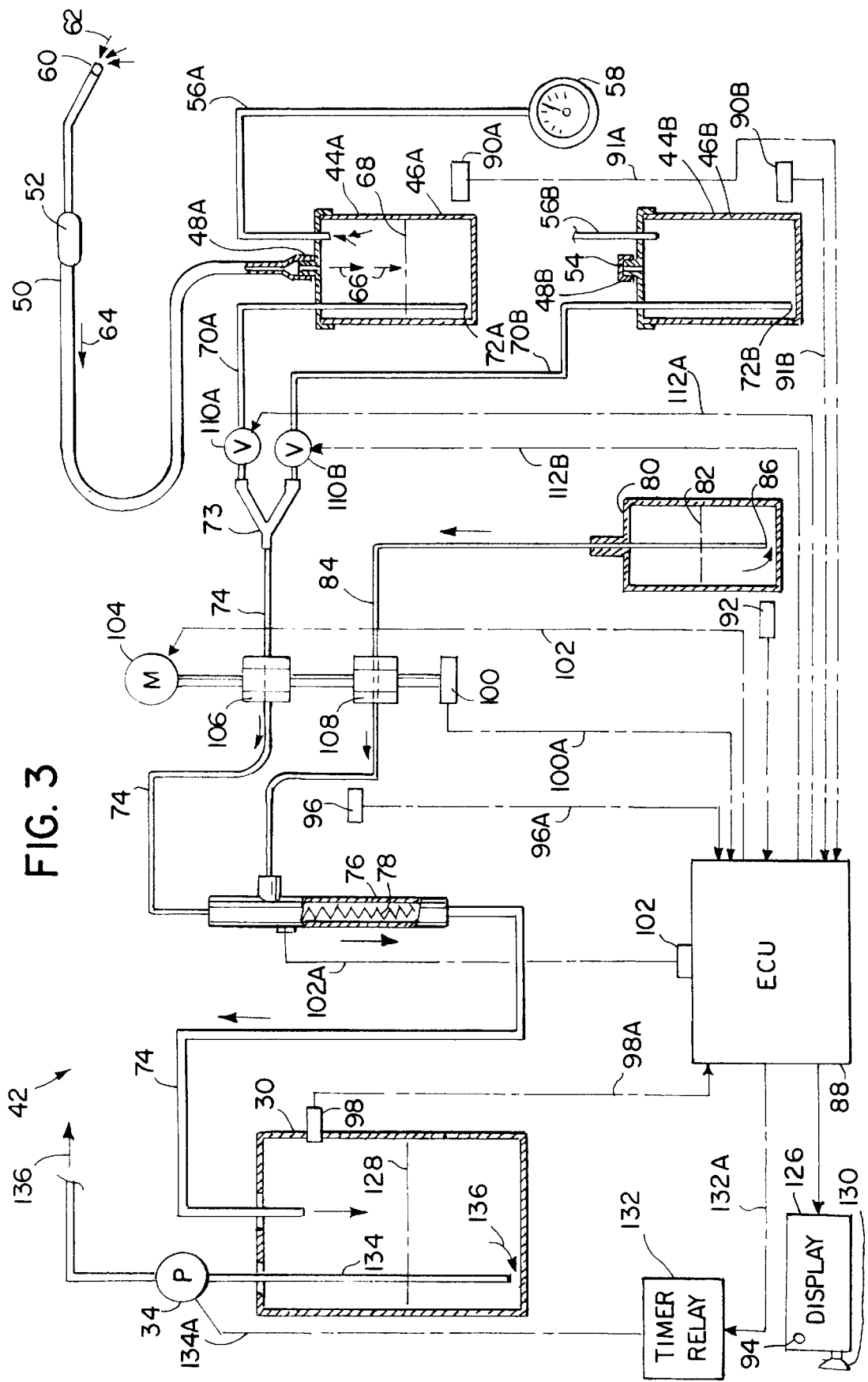
FIG. 3 is a schematic drawing illustrating the preferred operation of a biohazardous liquid waste collection and treatment system in accordance with the invention.

FIGS. 1 and 2 show a biohazardous liquid medical waste collection and treatment station 10 in accordance with the invention. The station 10 includes an upper unit 12 and a lower unit 14 that is detachable from the upper unit 12. Wheels 16 are mounted on the bottom surface of the upper unit 12 and wheels 18 are mounted on the bottom surface of the lower unit 14 so that the station 10 can easily roll over a floor 20. In addition, the wheels 16, 18 enable the lower unit 14 and the upper unit 12 to easily roll over a floor 20 when the units 14, 16 are detached from each other.

In FIG. 1, the lower unit 14 is physically attached to the upper unit 12, and is also electrically connected to the upper unit 12. In FIG. 2, the lower unit 14 is physically detached from the upper unit 12, and is also electrically disconnected from the upper unit 12. Latches 22 are used to physically attach the lower unit 14 to the upper unit 12. A multi-conductor electrical cord 24 is permanently attached to lower unit 14. The upper unit 12 has an electrical receptacle 26 which provides a port for DC electrical power and control signals transmitted from the upper unit 12. The multi-conductor electrical cord 24 on the lower unit 14 has a mating receptacle 28 that can be removably connected to the electrical receptacle 26 on the upper unit 12.

When the station 10 is being used to collect liquid medical waste, the upper unit 12 and the lower unit 14 are normally physically attached and electrically connected as shown in FIG. 1. Treated liquid waste is collected eventually in a treated waste temporary storage receptacle 30 located on the lower unit 14. A sight tube 32 is provided on the lower unit 14 so that a surgeon or other health care worker can visually monitor the treated liquid waste collected in the receptacle 30 in the lower unit 14. It may be desirable to provide markings along the sight tube 32 to facilitate visual gauging of the level of treated waste in the lower unit 14.

When the receptacle 30 in the lower unit 14 is full, or it is otherwise desirable to empty treated liquid waste from the lower unit 14, the lower unit 14 is physically detached from the upper unit 12 and also electrically disconnected from the upper unit 12 as shown in FIG. 2. A treated waste discharge pump 34 on the lower unit 14 discharges treated liquid waste from the receptacle 30 in the lower unit 14 to empty the receptacle 30. The treated waste discharge pump 34 is preferably an electrically driven peristaltic pump. The peristaltic pump 34 and the pump drive are preferably hinge mounted on the lower unit 14. Arrow 36 in FIG. 2 indicates that the pump 34 and the pump drive have been rotated upward into the position shown in FIG. 2. The pump drive is located in a pump control box 38 which includes an electrical receptacle 40. The mating electrical receptacle 28 on the multi-conductor electrical cord 24, which is permanently attached to the lower unit 14, is removably connected to the receptacle 40 on the pump control box 38 to provide power and control the operation of the liquid waste discharge pump 34.

FIG. 3 illustrates the preferred method in which the station 10 collects and treats biohazardous liquid medical waste. Referring to FIG. 3, a biohazardous liquid waste collection and treatment system 42 in accordance with the invention includes one or more suction chambers 44a, 44b. Each suction chamber 44a, 44b includes an internal liquid waste receptacle 46a, 46b and a liquid waste intake port 48a, 48b. A conventional suction tube 50, including a filter 52, is attached to liquid waste intake port 48a for suction chamber 44a. Suction chamber 44a is connected via tube 56a to a vacuum source 58. When the tip 60 of the suction tube 50 is located in body fluids, the vacuum source 58 creates a vacuum in the suction chamber 44a that aspirates the body fluids through the tip 60 into the tube 50 (arrow 62) and further draws the body fluids through the suction tube 50 (arrow 64) into the suction chamber 44a (arrow 66). In FIG. 3, suction chamber 44b is not used and therefore vacuum tube 56b is not connected to the vacuum source 58, and the liquid waste intake port 48b on suction chamber 44b is covered with cap 54. However, suction chamber 44b can be easily put into use by connecting vacuum tube 56b to the vacuum source 58 and connecting a suction tube such as suction tube 50 to the liquid waste intake port 48b.

The level of untreated liquid waste contained in the internal liquid waste receptacle 46a of the suction chamber 44a is represented by dash line 68. Tubing 70a extends into the suction chamber 44a. An open end 72a of the tube portion 70a is located near the bottom surface of the internal liquid waste receptacle 46a of the suction chamber 44a. Likewise, tubing 70b extends into the suction chamber 44b, and the open end 72b of tubing 70b is also in close proximity to the bottom of the internal liquid waste receptacle 46b of the suction chamber 44b. Tubing portions 70a and 70b are untreated liquid waste tube portions 70a and 70b which merge together at Y-fitting 73, and lead into a main tube portion 74.

A motionless mixer 76 containing baffles 78, such as a low viscosity stata-tube mixer sold by Kah Industries, Inc., Robinsville, N.J., is installed inline in the main tube portion 74. Downstream of the motionless mixer 76, the main tube portion 74 continues to a treated waste temporary storage receptacle 30.

The system 42 also includes a liquid disinfectant reservoir 80, which contains a supply of liquid disinfectant 82 for treating liquid waste. Various liquid waste disinfectants can be used in the system 42. Typical disinfectants include phenyl solutions, and chlorine-based disinfectants. A liquid disinfectant tube portion 84 extends into the liquid disinfectant reservoir 80. An open end 86 of the liquid disinfectant tube portion 84 is located close to the bottom surface of the liquid disinfectant reservoir 80. The liquid disinfectant tube 84 extends from the liquid disinfectant reservoir 80 and leads into the main tube portion 74. The liquid disinfectant tube 84 enters the main tube 74 downstream of the location 73 where the untreated liquid waste tube portions 70a, 70b enter the main tube 74 and upstream of the location that the motionless mixer 76 is installed in the main tube 74.

An electronic control unit 88 controls the operation of the system 42 based on input from several sensors. The sensors shown in FIG. 3 include proximity sensors 90a, 90b, 92, 96 and 98, shaft rpm sensor 100, and pressure sensor 102. Based on signals from these sensors, the electronic control unit 88 outputs an upper unit pump drive control signal through line 102 to pump drive 104. The pump drive 104 contemporaneously drives both a liquid waste pump 106 and a liquid disinfectant pump 108. In the preferred embodiment of the invention, both the liquid waste pump 106 and the liquid disinfectant pump 108 are peristaltic pumps, although other types of pumps may be used. For instance, disposable magnetized impeller pumps may be used.

The liquid waste pump 106 pumps liquid waste through the main tube portion 74 from the Y-fitting 73 to the motionless mixer 76. The liquid disinfectant pump 108 pumps liquid disinfectant through conduit 84 from the liquid disinfectant reservoir 80 to the mixer 76. Alternatively, liquid disinfectant tube portion 84 may lead into the main tube portion 74 slightly upstream of the mixer 76, see FIG. 4. In the preferred embodiment of the invention, the pump drive 104 and the pump heads 106, 108 are peristaltic pumps sold by the Barnant Company, Barrington, Ill., under the registered trademark MASTERFLEX®. The drive 104 is preferably a variable speed drive that receives DC electrical power (e.g. 12–24 volts DC) and provides an output speed of 10–500 rpm. The pump heads 106, 108 are preferably standard or cartridge-type easy load pump heads. The liquid waste main tube portion 74 is loaded into the liquid waste peristaltic pump 106 and the liquid disinfectant tube portion 84 is loaded into the liquid disinfectant peristaltic pump 108 prior to system 42 operation. Because the liquid waste peristaltic pump 106 and the liquid disinfectant peristaltic pump 108 are driven by a common pump drive 104, an appropriate amount of disinfectant to assure proper treatment of the liquid medical waste aspirated from the patient can be easily metered by selecting the appropriate relative tube sizes for the main tube portion 74 in relation to the liquid disinfectant portion 84. For instance, in the case where the disinfectant manufacturers recommend one ounce of liquid disinfectant to one gallon of liquid medical waste, it is preferred that the tube portion 74, 84 be made of TYGON® with the liquid disinfectant tube 84 having a 3/16 inch inside diameter and a 5/16 inch outside diameter, and the liquid waste tube 74 having a 5/16 inch inside diameter and a 7/16 inch outside diameter. Proper selection of the respective peristaltic tube portions 74, 84 assures that a sufficient amount of liquid disinfectant is mixed with the biohazardous liquid medical waste over the full range of pump speeds, and also helps eliminate wasting excessive amounts of liquid disinfectant by over treating, especially at low flow rates. FIG. 7 shows the liquid waste tube portion 74 and the liquid disinfectant tube portion 84 being loaded in the liquid waste pump 106 and the liquid disinfectant pump 108, and illustrates the relative cross-sections of the tube portions 74, 84.

Proximity sensors 90a, 90b monitor the level of liquid waste in the internal liquid waste receptacles 46a, 46b in the respective suction chambers 44a, 44b. In particular, the proximity sensors 90a, 90b detect whether the liquid waste in the respective liquid waste receptacle 46a, 46b is above a threshold liquid waste level. Proximity sensor 90a transmits a signal through line 91a to the electronic control unit 88, and proximity sensor 90b transmits a signal through line 91b to the electronic control unit 88. The electronic control unit 88 transmits signals through lines 112a and 112b to control the operation of valves 110a and 110b in response to the signals from the proximity switches 90a, 90b. Valves 110a and 110b control flow through the untreated liquid waste tube portions 70a, 70b upstream of the Y-fitting 73.

The valves 110a and 110b are normally closed. Valve 110a and/or valve 110b are opened when the respective proximity sensor 90a, 90b detects liquid waste in the respective liquid waste receptacle 46a, 46b at a level above the threshold level. In FIG. 3, the level of liquid waste 68 in suction chamber 44a is above the threshold level, and therefore the electronic control unit 88 transmits a signal through line 112a to open valve 110a. On the other hand, suction chamber 44b is empty as shown in FIG. 3, and therefore valve 110b remains closed. If either proximity sensor 90a or 90b senses liquid waste in the respective suction chamber 44a, 44b, the electronic control unit 88 also transmits a control signal through line 102 to actuate pump drive 104. When the pump drive 104 is actuated, the liquid waste pump 106 draws untreated liquid waste from the respective suction chambers 44a, 44b in accordance with the position (i.e. open or closed) of the valves 110a, 110b. In the situation depicted in FIG. 3, liquid waste pump 106 draws untreated liquid waste from suction chamber 44a because valve 110a is open, but does not draw any liquid waste from suction chamber 44b. It is important that valve 110b be closed if there is no liquid waste within the suction chamber 44b, otherwise liquid pump 106 will not operate properly to draw liquid waste from suction chamber 44a. If liquid waste were present in suction chamber 44b above the threshold liquid waste level, electronic control unit 88 would transmit a signal through line 112b to open valve 110b, thus allowing the liquid waste pump 106 to draw liquid waste from both suction chambers 44a and 44b, preferably in equal proportions. By locating the pump 106 downstream of the Y-fitting 73 and downstream of the valves 110a, 110b, a single liquid waste pump 106 driven in unison with the liquid disinfectant pump 108 ensures that the preselected ratio of liquid disinfectant is mixed with the pumped liquid waste in correct proportions, whether the system 42 is using one suction chamber 44a to aspirate surgical fluids or two or more suction chambers to aspirate surgical fluids.

Valves 110a, 110b are preferably electrically driven solenoid valves. FIGS. 5 and 6 show the operation of solenoid valves 110a, 110b for the situation shown in FIG. 3 where solenoid valve 110a is open and solenoid valve 110b is closed. Each solenoid valve 110a, 110b includes a valve head 114a, 114b that is displaced by a shaft 116a, 116b driven by an electrically powered cylinder 118a, 118b. Tube portions 70a, 70b are mounted between the respective valve head 114a, 114b and a common valve plate 120. The valve plate 120 is attached to the valve structure using screws 124. With tube portion 70a, 70b positioned properly between the respective valve head 114a, 114b and the valve plate 120, the solenoid valves 110a, 110b can effectively close and seal the respective tube portions 70a, 70b by displacing the respective valve head 114a, 114b to pinch the tube portion 70b between the valve head 114b and the valve plate 120.

Proximity sensors 92, 96 and 98 and pressure sensor 102 are used to shut off system operation when unfavorable operating conditions exist. Proximity sensor 92 monitors the level of disinfectant 82 within the liquid disinfectant reservoir 80, and transmits a signal in response thereto to the electronic control unit 88. The electronic control unit 88 outputs a signal to display 126 which provides a warning when the disinfectant level in the reservoir 80 starts to become low. If the level of liquid disinfectant 82 in the reservoir 80 falls below a minimum threshold value, the electronic control unit 88 suspends operation of the pump drive 104.

Proximity sensor 96 monitors whether liquid disinfectant is present in the liquid disinfectant tube portion 84 downstream of the liquid disinfectant pump 108 and transmits a signal in response thereto through line 96a to the electronic control unit 88. Electronic control unit 88 disables system 42 operation if liquid disinfectant is not present in the tube portion 84 downstream of the pump 108. In addition, proximity sensor 96 is used to determine whether liquid disinfectant pump 108 is properly primed at system start-up prior to system operation. The display 126 includes a run prime button 94 which when actuated manually overrides the electronic control unit 88 to operate pumps 106 and 108 so that the liquid disinfectant pump 108 draws liquid disinfectant from the liquid disinfectant reservoir to properly prime the pump 108 before system operation.

A pressure tap tube 102a is connected to the main tube 74 upstream of the motionless mixer 76. The pressure tap tube 102a leads to a pressure sensor 102 located at the electronic control unit 88. The pressure sensor 102 monitors the liquid pressure upstream of the mixer 76. Excessive mixing chamber pressure can indicate clogging in the motionless mixer 78. It is preferred to display the mixing chamber pressure on the display 126. It is also preferable to disable system 42 operation when mixing chamber pressure becomes excessive.

Proximity sensor 98 senses the level of the mixture of liquid medical waste and liquid disinfectant 128 in the treated waste temporary storage receptacle 30. The proximity sensor 98 is preferably a capacitive-type proximity sensor which provides a signal through line 98a to the electronic control unit 88. In response to the signal in line 98a from the proximity sensor 98, the electronic control unit 88 provides information to the display 126 which includes both a visual indication that the treated waste tank is becoming full and an audio alarm 130 which is preferably actuated when the receptacle 30 is becoming full. Also, the electronic control unit 88 disables system operation when the treated waste temporary storage receptacle 30 becomes completely full. It is preferred that the alarm 130 output an audible signal with increasing frequency as the treated waste temporary storage receptacle 30 becomes closer to being completely full.

The system 42 also includes an rpm sensor/encoder 100 which monitors the speed of pumps 106, 108, and transmits a signal in response thereto through line 100a to the electronic control unit 88. Based on the signal in line 100a from the rpm sensor/encoder 100, the electronic control unit 88 determines the amount of total fluid processed during any single surgery. It is desirable to display both instantaneous pump speed and total amount of fluid processed on the display 126. In addition, based on the signal in line 100a from the rpm sensor/encoder 100, the electronic control unit 88 provides a pump timing signal through line 132a to timer relay 132.

The timer relay 132 controls the operation of the treated waste discharge pump 34 via line 134a. The timer relay 132 is pre-programmed with a preselected disinfectant treatment time period (e.g. 10 minutes, although manufacturer recommendations should be followed). The timer relay 132 is wired to the electrical power source for the treated waste discharge pump 34. The timer relay postpones operation of the treated waste discharge pump 34 for the preselected disinfectant treatment time period since the most recently detected movement of the pump 106 by encoder 100. In this manner, the treated waste discharge pump 34 cannot be actuated to discharge the mixture of liquid medical waste and liquid disinfectant 128 from the treated waste temporary storage receptacle 30 through pump discharge tube 134 (arrows 136) until all of the mixture 128 in the receptacle 30 has coexisted in the receptacle 30 for at least the preselected disinfectant treatment time period.

FIGS. 4–15 illustrate various details of the biohazardous liquid medical waste collection and treatment station 10 shown in FIGS. 1 and 2 which preferably operates in accordance with the control schemes shown in FIG. 3.

Figure 8:
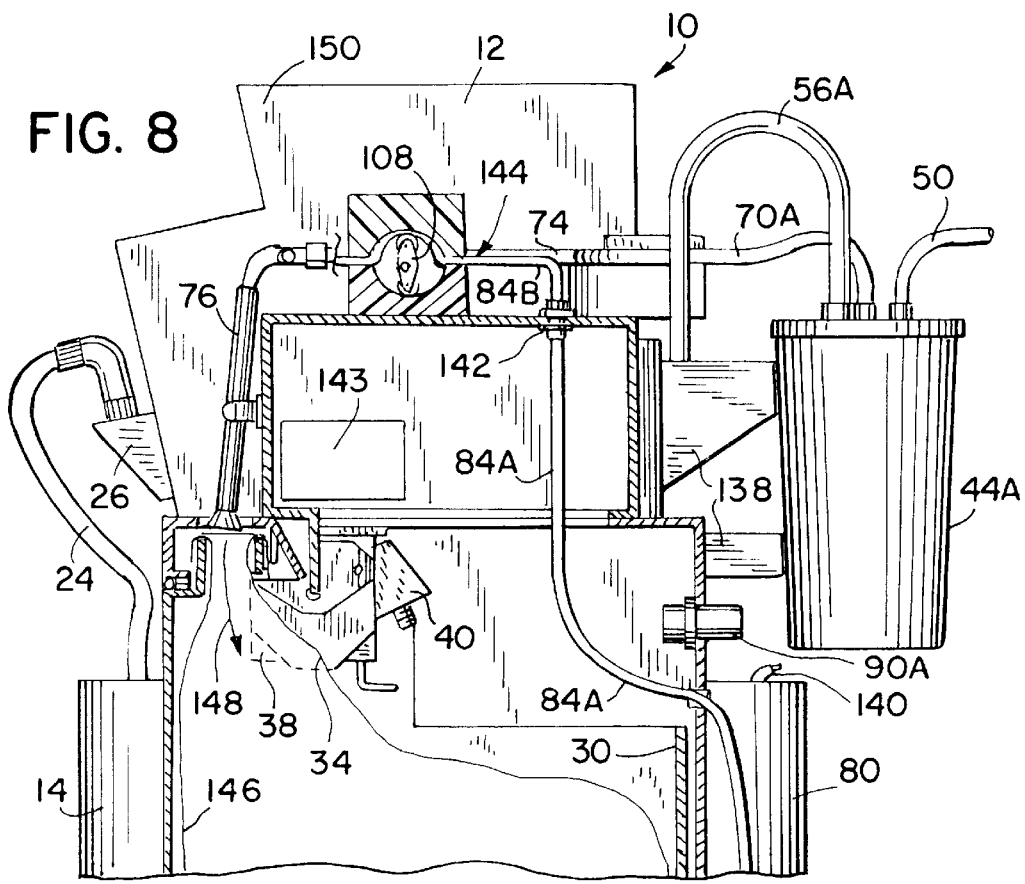
FIG. 8 is a view taken along line 8—8 in FIG. 4.

Referring now in particular to FIGS. 4 and 8, the suction chambers 44a, 44b, and 44c are preferably similar to or identical to conventional disposable suction canisters. However, the suction canisters 44a, 44b, and 44c are not connected in series to one another. The suction chambers 44 are connected to the upper unit 12 individually, using a plastic bracket 138.

The liquid disinfectant reservoir 80 on the upper unit 12 includes a filling port 140 to facilitate the filling of the liquid disinfectant reservoir 80. The liquid disinfectant tube portion 84 from the reservoir 80 to the pump 108 includes portion 84a, and 84b which are connected together by a quick disconnect fitting 142. The portion 84a is permanently installed on the upper unit 12. The portion 84a is preferably part of a disposable tube set 144.

It is preferred that the disposable tube set 144 be replaced for each patient. The disposable tube set 144 preferably includes the main tube portion 74, one or more untreated liquid waste tube portions 70a, 70b leading into the main tube portion 144, the liquid disinfectant tube portion 84b leading into the main tube portion 74 and the motionless mixer 76 installed in the main tube portion 74. The untreated liquid waste tube portion 70a, 70b have quick disconnect inlets so that they may be quickly and easily connected to the respective liquid suction chambers 44a, 44b. Likewise, the liquid disinfectant tube portion has the quick connect inlet 142 as previously mentioned. The integral tube set also preferably includes pressure tap tube portion 102a having a quick disconnect inlet to the pressure sensor 102.

Figure 9:
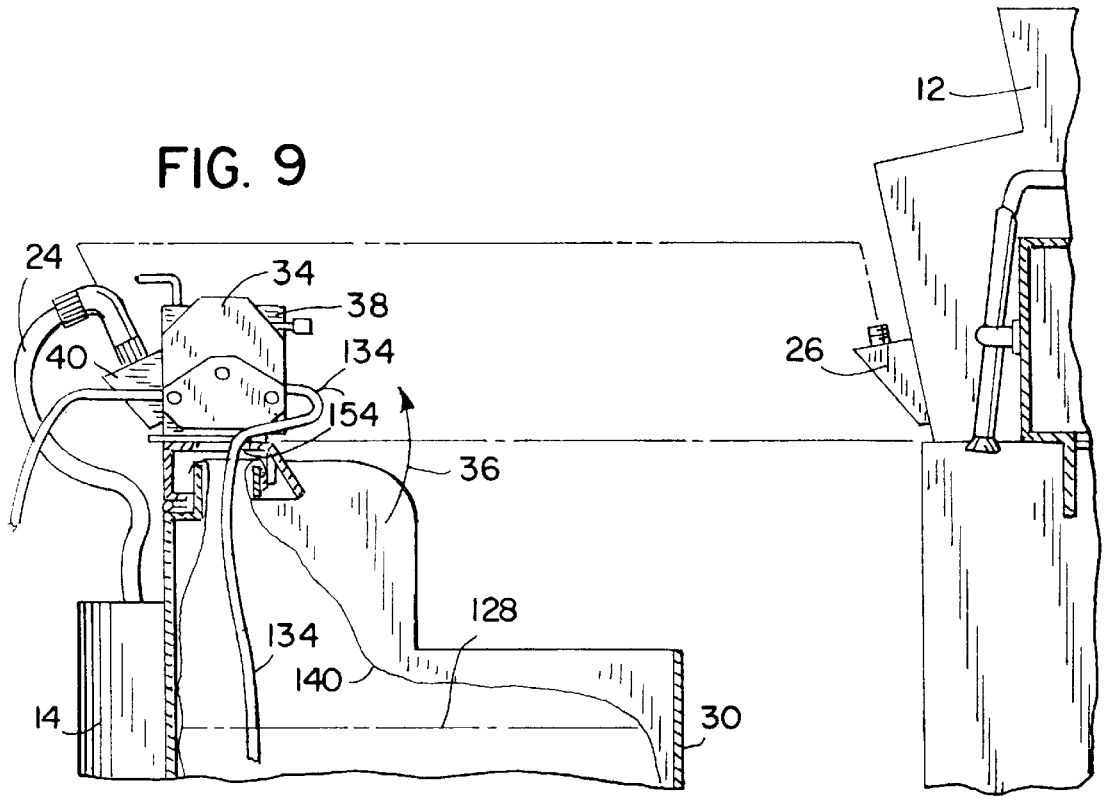
FIG. 9 is a view illustrating the operation of a treated waste discharge pump when the lower unit is detached from the upper unit as in accordance with the preferred embodiment of the invention.

When the upper unit 12 and the lower unit 14 are attached to collect liquid waste, it is desirable to provide a plastic liner 146 in the treated waste contemporary storage receptacle 30 on the lower unit 14 to receive the mixture of liquid waste and liquid disinfectant from the disposable tube set 144 (arrow 148). In FIG. 8, the hinge mounted discharge pump control box 38 and discharge pump 34 are in the down position. Hinge mounting means components facilitates compact design of the station 10. FIG. 9 shows the lower unit 14 detached from the upper unit 12 in preparation for discharging treated waste from the treated waste temporary storage receptacle 30 in the lower unit 14. In FIG. 9, the discharge pump control box 38 and discharge pump 34 are rotated to the up position.

The upper unit 12 includes a control box 141 which houses the electrical and electronic components on the upper unit 12. In particular, the control box 141 on the upper unit 12 contains the electronic control unit 88 and a battery charger 143. The battery charger 143 is used to charge batteries 145, FIG. 14, on the lower unit 14 when the multi-conductor electrical cord 24 on the lower unit 14 is connected to the electrical receptacle 26 on the upper unit 12. The upper unit 12 includes a cover 150. The cover 150 should be closed during system operation. Opening the cover 150 preferably actuates a switch to disable operation of the upper unit 112.

FIGS. 10–13 illustrate the preferred splashguard on the lower unit 14. The splashguard is used to support the plastic liner 146 within the treated waste temporary storage receptacle 30. To install the plastic liner 146, the splashguard cover 152 is opened and the top edge of the plastic liner 146 is placed over a splashguard ring 150. The splashguard cover 152 includes a friction wheel which holds the plastic liner 146 in place when the cover 152 is closed, FIG. 10, by squeezing the plastic liner 146 against the splash ring 150. The cover 152 includes an opening 154 that allows access for the pump discharge tube 134 into the plastic liner 146 in the lower unit receptacle 30. Besides the access hole 154, the cover 152 isolates the treated liquid waste 128 within the plastic liner 146 from the outside environment.

FIG. 9 not only shows the discharge pump control box 38 and the discharge pump 34 rotated upward (arrow 36), but also shows the discharge pump control box 38 and discharge pump 34 connected to VDC electrical power via line 24. DC power is provided to cord 24 from batteries 145 on the lower unit, FIG. 14. The batteries 145 on the lower unit 14 are able to provide DC electrical power to the discharge pump control box 38 when the lower unit 14 is disconnected from the upper unit 12. Therefore, treated liquid waste can be discharged when the lower unit 14 is remote from both the upper unit 12, and/or remote from the other electrical power sources. The batteries 145 on the lower unit 14 shown in FIG. 14, are charged by the battery charger 143 on the upper unit 12 when the lower unit 14 and the upper unit 12 are electrically connected. FIG. 14 also shows the timer relay 132 that ensures that electrical power from the batteries 145 is not supplied to the discharge pump control box 38 until the preselected disinfectant treatment time period (e.g. 10 minutes) has elapsed.

In accordance with the invention, it is desirable that the station 10 include more than one lower unit 14. By providing more than one lower unit 14, the station 10 can continue to collect liquid medical waste uninterrupted with unlimited capacity. This can be accomplished by replacing a first lower unit 14 when it becomes full with another lower unit 14 that is empty. The capacity in the disposable suction chambers 44a, 44b, and 44c is sufficient under normal conditions to provide enough time for the replacement of lower units 14 without interrupting aspiration. By the time the second lower unit is full, the first lower unit 14 should be fully discharged and ready for use. This cycle can continue as necessary.

FIG. 15 dramatically illustrates the preferred display panel 126. The display panel 126 preferably includes indicator lights 156a through 156e. Indicator light 156a is illuminated when pressure sensor 102 senses that excessively high pressure is present in the motionless mixer 76. Indicator light 156b is illuminated when the proximity sensor 92 senses that the level 82 of liquid disinfectant in the liquid disinfectant reservoir 80 is becoming low. Indicator light 156c illuminates when cover 150 is open. Indicator light 156d illuminates when the treated waste temporary storage receptacle 30 in the lower unit 14 is full. Indicator light 156e illuminates when proximity sensor 96 senses that insufficient liquid disinfectant is present in line 84 downstream of the liquid disinfectant pump 108.

The display panel 126 also includes digital readouts 158a through 158c. Digital readout 158a displays the total amount of fluid processed for the patient. Digital readout 158b displays the liquid pressure in the motionless mixer 76. Digital readout 158c displays instantaneous pump speed. The display panel 126 also preferably includes a speed control knob 160 to control the speed of the pump drive 104 which contemporaneously drives both the liquid waste pump 106 and the liquid disinfectant pump 108.

The display panel 126 preferably includes battery indicator lights 162a, 162b which are illuminated to indicate whether the battery is charging or full, respectively. As mentioned above, the display 126 also includes a run/prime button 94 and an audible alarm 130. The run/prime button is used to override the control of the electronic control unit 88 at system start-up when it is important to prime the liquid disinfectant pump 108. The audible alarm 130 mounted to the control panel is useful because surgeons or other health care workers may be concentrating on other matters when the system is in use. It may be desirable to provide audible signals having distinctive characteristics to audibly signal various system information to surgeons and other health care workers.

The drawings illustrate a preferred embodiment of the invention, and various alternatives, modifications, and equivalents to the invention may be apparent to those skilled in the art. Such alternatives, modifications and equivalents which do not depart from the spirit of the invention, should be considered to fall within the scope of the following claims.

I claim:

1. A biohazardous liquid waste collection and treatment system comprising:
    a suction chamber including an internal liquid waste receptacle and a liquid waste intake port;
    a suction tube connected to the liquid waste intake port on the suction chamber;
    a vacuum source connected to the suction chamber that creates a vacuum in the suction chamber to draw liquid waste through the suction tube into the internal liquid waste receptacle in the suction chamber;
    a liquid disinfectant reservoir;
    a waste treatment mixer;
    a liquid waste pump that pumps liquid waste from the internal liquid waste receptacle in the suction chamber to the waste treatment mixer;
    a liquid disinfectant pump that pumps liquid disinfectant from the liquid disinfectant reservoir to the waste treatment mixer; and
    a treated waste temporary storage receptacle that receives a mixture of liquid waste and liquid disinfectant from the waste treatment mixer;
    wherein said system is configured and arranged such that the liquid waste pump and the liquid disinfectant pump simultaneously pump the liquid waste and the liquid disinfectant to the waste treatment mixer.

2. A biohazardous liquid waste treatment system as recited in claim 1 further comprising:
    a first portion of tubing extending from the internal liquid waste receptacle in the suction chamber to the waste treatment mixer; and
    a second portion of tubing extending from the liquid disinfectant reservoir to the waste treatment mixer; and
    wherein the liquid waste pump is a peristaltic pump that pumps liquid waste through the first portion of tubing, and the liquid disinfectant pump is a peristaltic pump that pumps liquid disinfectant through the second portion of the tubing.

3. A biohazardous liquid waste treatment system as recited in claim 2 further comprising:
    a third portion of tubing that receives the mixture of the liquid waste and liquid disinfectant from the waste treatment mixer and empties the mixture into the treated waste temporary storage receptacle.

4. A biohazardous liquid waste treatment system as recited in claim 3 wherein the waste treatment mixer and the first, second and third portion of tubing are components of an integral apparatus that is disposable.

5. A biohazardous liquid waste treatment system as recited in claim 2 further comprising a pump drive that contemporaneously drives both the liquid waste peristaltic pump and the liquid disinfectant peristaltic pump, and wherein the size of the first portion of the tubing and the size of the second portion of the tubing are selected to meter the amount of liquid disinfectant flowing to the waste treatment mixer through the second portion of tubing in proportion to the amount of untreated liquid waste flowing to the waste treatment mixer through the first portion of tubing.

6. A biohazardous liquid waste treatment system as recited in claim 1 wherein the waste treatment mixer is a mixer containing baffles.

7. A biohazardous liquid waste treatment system as recited in claim 1 further comprising an electronic controller that outputs one or more waste treatment control signals to control the operation of the liquid waste pump and the liquid disinfectant pump.

8. A biohazardous liquid waste treatment system as recited in claim 7 further comprising an untreated liquid waste sensor that senses whether the level of liquid waste in the internal liquid waste receptacle in the suction chamber is above a threshold liquid waste level and generates a waste level signal in response thereto that is transmitted to the electronic controller;
    wherein the electronic controller outputs one or more of the waste treatment control signals to activate the liquid waste pump and the liquid disinfectant pump only when the level of liquid waste in the internal liquid waste receptacle in the suction chamber is above the threshold liquid waste level.

9. A biohazardous liquid waste treatment system as recited in claim 7 further comprising:
    a liquid disinfectant prime sensor that senses whether the liquid disinfectant pump is primed and generates a liquid disinfectant prime signal in response thereto that is transmitted to the electronic controller;
    wherein the electronic controller outputs one or more of the waste treatment control signals to activate the liquid waste pump only when the liquid disinfectant pump is primed.

10. A biohazardous liquid waste treatment system as recited in claim 1 further comprising:
    a treated waste discharge pump that pumps the mixture of liquid waste and liquid disinfectant from the treated waste temporary storage receptacles.

11. A biohazardous liquid waste treatment system as recited in claim 10 further comprising:
    means for determining operation of the liquid waste pump for pumping liquid waste from the internal liquid waste receptacle through the mixer and into the treated waste temporary storage receptacle and generating a signal in response thereto;
    a timing means for postponing operation of the treated waste discharge pump until expiration of a preselected disinfectant treatment time period, said timing means receiving the signal from the means for determining operation of the liquid waste pump and being reset whenever the liquid waste pump operates to pump liquid waste from the internal liquid waste receptacle through the mixer and into the treated waste temporary storage receptacle.

12. A biohazardous liquid waste treatment system as recited in claim 10 further comprising:

means for sensing flow of the mixture of liquid waste and liquid disinfectant from the waste treatment mixer into the treated waste temporary storage receptacle and generating a signal in response thereto; and timing means for postponing operation of the treated waste discharge pump until expiration of a preselected disinfectant treatment time period, said timing means receiving the signal from said sensing means and being reset whenever the mixture of liquid waste and liquid disinfectant flows into the treated waste temporary receptacle.

13. A biohazardous liquid waste treatment system as recited in claim 12 wherein the sensing means for sensing flow of the mixture of liquid waste and liquid disinfectant from the waste treatment mixer into the treated waste temporary storage receptacle is a proximity sensor.

14. A biohazardous liquid waste treatment system as recited in claim 12 wherein the sensing means for sensing flow of the mixture of liquid disinfectant from the waste treatment mixer into the treated waste temporary storage receptacle includes means for determining whether the liquid waste pump is operating to pump liquid waste from the internal liquid waste receptacle.

15. A biohazardous liquid waste treatment system as recited in claim 1 wherein the recited suction chamber is a first suction chamber and the recited suction tube is a first suction tube and the system further comprises:

a second suction chamber including an internal liquid waste receptacle and a liquid waste intake port, wherein the vacuum source is also connected to the second suction chamber to create a vacuum in the second suction chamber;

untreated liquid waste tubing including a main portion entering the liquid waste pump, a first branch portion extending from the internal liquid waste receptacle in the first suction chamber to the main portion, and a second branch portion extending from the internal liquid waste receptacle in the second suction chamber to the main portion;

a first valve that opens and closes the flow path through the first branch portion of the untreated liquid waste tubing; and a second valve that opens and closes the second branch portion of the untreated liquid waste tubing.

16. A biohazardous liquid waste treatment system as recited in claim 15 further comprising:

an electronic controller that outputs one or more pump control signals to control the operation of the liquid waste pump and also outputs a first valve control signal to open and close the first valve for the first branch portion of the untreated liquid waste tubing and a second valve control signal to open and close the second valve for the second branch portion of the untreated liquid waste tubing;

a first untreated liquid waste sensor that senses whether the level of liquid waste in the internal liquid waste receptacle in the first suction chamber is above a first threshold liquid waste level and generates a first waste level signal in response thereto that is transmitted to the electronic controller;

a second untreated liquid waste sensor that senses whether the level of liquid waste in the internal liquid waste receptacle in the second suction chamber is above a second threshold liquid waste level and generates a second waste level signal in response thereto that is transmitted to the electronic controller;

wherein the electronic controller outputs the first valve control signal to open the first valve only when the level of liquid waste in the internal liquid waste receptacle for the first suction chamber is above the first threshold liquid waste level and the electronic controller outputs the second valve control signal to open the second valve only when the level of liquid waste in the internal liquid waste receptacle in the second suction chamber is above the second threshold liquid waste level.

17. A biohazardous liquid waste treatment system as recited in claim 1 further comprising a pump drive mechanism that drives both the liquid waste pump and the liquid disinfectant pump contemporaneously.

18. A biohazardous liquid waste treatment system as recited in claim 1 further comprising:

a liquid waste pump rpm sensor that senses the speed of the liquid waste pump and generates a liquid waste pump speed signal in response thereto; and a display that receives the liquid waste pump speed signal and indicates the liquid waste pump speed in response thereto.

19. A biohazardous liquid waste treatment system as recited in claim 1 further comprising a liquid disinfectant pump rpm sensor that senses the speed of the liquid disinfectant pump and generates a liquid disinfectant pump speed signal in response thereto; and a display that receives the liquid disinfectant pump speed signal and indicates the liquid disinfectant pump speed in response thereto.

20. A biohazardous liquid waste treatment system as recited in claim 1 further comprising a pressure sensor that senses liquid pressure in the mixer and generates a signal in response thereto; and a display that receives a signal from the pressure sensor and indicates the pressure in response thereto.

21. A biohazardous liquid waste treatment system as recited in claim 1 further comprising means for measuring the amount of liquid waste pumped through the liquid waste pump; and means for displaying the amount of liquid waste pumped through the liquid waste pump.

22. An on-site biohazardous liquid waste and collection and treatment station comprising an upper unit and a lower unit that is detachable from the upper unit, wherein:

the upper unit includes:

a suction chamber including an internal liquid waste receptacle and a liquid waste intake port;

a suction tube connected to the liquid intake port on the suction chamber;

a vacuum port adapted to be connected to a vacuum source, the vacuum port communicating with the suction chamber to enable the creation of a vacuum in the suction chamber to draw liquid waste through the suction tube into the internal liquid waste receptacle in the suction chamber;

a liquid disinfectant reservoir;

a waste treatment mixer;

a liquid waste pump that pumps liquid waste from the internal liquid waste reservoir in the suction chamber to the waste treatment mixer;

means for providing liquid disinfectant from the liquid disinfectant reservoir to the waste treatment mixer; and the lower unit includes:

a treated waste temporary storage receptacle that receives a mixture of liquid waste and liquid disinfectant from the waste treatment mixer.

23. An on-site biohazardous liquid waste collection and treatment station as recited in claim 22 wherein the means for providing liquid disinfectant from the liquid disinfectant reservoir to the waste treatment mixer is a liquid disinfectant pump.

24. An on-site biohazardous liquid waste collection and treatment station as recited in claim 23 further comprising a disposable tube set including a main tube portion in which the waste treatment mixer is installed, an untreated liquid waste tube portion extending from the internal liquid waste receptacle in the suction chamber and leading to the main tube portion, a liquid disinfectant tube portion extending from the liquid disinfectant reservoir and leading to the main tube portion; and wherein the liquid waste pump is a peristaltic pump that pumps liquid waste through the untreated liquid waste tube portion and the liquid disinfectant pump is a peristaltic pump that pumps liquid disinfectant through the liquid disinfectant tube portion.

25. An on-site biohazardous liquid waste collection and treatment station as recited in claim 22 wherein the means for providing liquid disinfectant from the liquid disinfectant reservoir to the waste treatment mixer involves placing the liquid disinfectant reservoir at a height above the waste treatment mixer so that liquid disinfectant is gravity fed from the liquid disinfectant reservoir to the waste treatment mixer.

26. An on-site biohazardous liquid waste collection and treatment station as recited in claim 22 wherein the lower unit includes a sight tube that enables visual monitoring of the liquid mixture in the treated waste temporary storage receptacle.

27. An on-site biohazardous liquid waste treatment station as recited in claim 26 wherein a visual gauge is marked on the lower unit adjacent the sight tube to facilitate visual monitoring of the level of the liquid mixture in the treated waste temporary storage receptacle.

28. An on-site biohazardous liquid waste collection and treatment station as recited in claim 22 wherein a plurality of wheels are mounted to the lower unit to enable rolling of the lower unit over a floor.

29. An on-site biohazardous liquid waste collection and treatment station as recited in claim 22 wherein the lower unit further includes:

means for determining the presence of flow of the mixture of liquid waste and liquid disinfectant from the waste treatment mixer into the treated waste temporary storage receptacle in the lower unit;

a treated waste discharge pump that pumps treated waste from the treated waste temporary storage receptacle;

control means for operating the treated waste discharge pump; and a timer relay that postpones operation of the treated waste discharge pump until expiration of a preselected disinfectant treatment time period, the timer relay being reset whenever the mixture of the liquid waste and liquid disinfectant flows into the treated waste storage receptacle in the lower unit.

30. An on-site biohazardous liquid waste collection and treatment station as recited in claim 29 wherein the means for determining the presence of flow of the mixture of liquid waste and liquid disinfectant into the treated waste temporary storage receptacle is contained in an electronic controller on the upper unit that controls operation of the liquid waste pump.

31. An on-site biohazardous liquid waste collection and treatment station as recited in claim 29 wherein the lower unit also includes an electrical power source that provides power to the treated waste discharge pump.

32. An on-site biohazardous liquid waste collection and treatment station as recited in claim 31 wherein the timer relay on the lower unit receives electrical power from the electrical power source on the lower unit.

33. An on-site biohazardous liquid waste collection and treatment station as recited in claim 29 wherein the upper unit includes:

an AC power receptacle;

a battery charger that receives AC electrical power from the AC power receptacle and outputs DC electrical power to a DC power receptacle on the upper unit; and the lower unit includes:

a battery;

a mating DC power receptacle adapted to be connected to the DC power receptacle on the upper unit; and a DC power cord from the mating DC power receptacle on the lower unit to the battery on the lower unit.

34. An on-site biohazardous liquid waste collection and treatment station as recited in claim 22 wherein the lower unit includes:

a proximity sensor that senses a level of the mixture of the liquid waste and liquid disinfectant in the treated waste temporary storage receptacle and generates a signal in response thereto; and the upper unit includes:

an alarm that activates when the treated waste temporary storage receptacle is full.

35. An on-site biohazardous liquid waste collection and treatment station as recited in claim 22 wherein the recited lower unit is a first lower unit and the station further comprises a second lower unit that is also detachable from the upper unit, the second lower unit including a treated waste temporary storage receptacle that receives a mixture of liquid waste and liquid disinfectant from the waste treatment mixer when the second lower unit is attached to the station.

36. An on-site biohazardous liquid waste collection and treatment station as recited in claim 35 wherein a plurality of wheels are mounted to the first lower unit to enable rolling of the first lower unit over a floor; and a plurality of wheels are mounted to the second lower unit to enable rolling of the second lower unit over a floor.

37. An on-site biohazardous liquid waste collection and treatment station as recited in claim 22 wherein the lower unit further includes:

a splashguard that supports a top end of a disposable plastic liner placed within the treated waste temporary storage receptacle; and a movable cover adapted to be placed over the top end of the disposable plastic liner when the disposable plastic liner is placed within the treated waste temporary storage receptacle and supported by the splashguard, the cover including an opening to allow access for a treated waste discharge tube into the disposable plastic liner placed within the treated waste temporary storage receptacle when the cover is placed over the top end of the disposable plastic liner.

38. An on-site biohazardous liquid waste collection and treatment station as recited in claim 37 wherein the lower unit further includes friction means to facilitate support of the top end of the disposable plastic liner by the splashguard.

39. An on-site biohazardous liquid waste collection and treatment station as recited in claim 22 wherein the upper unit includes:

an electronic controller that controls operation of the liquid waste pump;

means for determining whether the lower unit is attached to the upper unit; and means for disabling operation of the liquid waste pump on the upper unit unless the lower unit is attached to the upper unit.

40. A method of treating a biohazardous liquid medical waste on-site comprising the steps of:

pumping biohazardous liquid waste from one or more suction chambers and contemporaneously flowing liquid disinfectant from a liquid disinfectant receptacle;

mixing the liquid disinfectant from the liquid disinfectant receptacle with the pumped liquid waste to form a mixture of liquid waste and liquid disinfectant;

flowing the mixture of liquid waste and liquid disinfectant into a treated waste temporary storage receptacle;

monitoring flow of the mixture of the liquid waste and liquid disinfectant into the treated waste temporary storage receptacle;

holding the mixture of liquid waste and liquid disinfectant in the treated waste temporary storage receptacle for a preselected disinfectant treatment time period after the instant in time that any amount of the mixture of liquid waste and liquid disinfectant has flowed into the treated waste temporary storage receptacle;

pumping the mixture of liquid waste and liquid disinfectant from the treated waste temporary storage receptacle after holding the mixture of liquid waste and liquid disinfectant in the treated waste temporary storage receptacle until expiration of the preselected disinfectant treatment time period.

41. A method as recited in claim 40 wherein the liquid disinfectant is a phenyl solution and the preselected disinfectant treatment time period is approximately ten minutes.

42. A method as recited in claim 40 wherein the liquid disinfectant is flowed from the liquid disinfectant receptacle by pumping the liquid disinfectant from the liquid disinfectant receptacle.

43. A method as recited in claim 42 wherein the liquid waste is pumped by a liquid waste pump and the liquid disinfectant is pumped by a liquid disinfectant pump and the method further comprises the steps of:

monitoring whether the liquid disinfectant pump is pumping liquid disinfectant; and disabling a liquid waste pump used to pump the liquid waste when the liquid disinfectant pump is not pumping liquid disinfectant.

44. A method as recited in claim 40 wherein the liquid disinfectant is flowed from the liquid disinfectant receptacle at least primarily by the force of gravity.

45. A method as recited in claim 40 further comprising the step of priming a pump used to pump the liquid disinfectant before contemporaneously pumping the liquid waste and the liquid disinfectant.

46. A method as recited in claim 40 wherein the liquid waste is pumped by a liquid waste pump, and the liquid waste and liquid disinfectant are thoroughly mixed in the mixer, and the method further comprises the steps of:

monitoring liquid pressure of the pumped liquid waste and the liquid disinfectant at a location upstream of the mixer; and disabling the liquid waste pump used to pump the liquid waste when the monitored liquid pressure upstream of the mixer exceeds a threshold pressure level.

47. A method as recited in claim 40 further comprising the steps of:

measuring the amount of liquid waste pumped;

displaying the measured amount of liquid waste pumped.

48. A method as recited in claim 40 further comprising the step of:

providing an alarm when the treated waste temporary storage receptacle is full of the mixture of liquid waste and liquid disinfectant.

49. A method as recited in claim 40 wherein the mixture of liquid waste and liquid disinfectant is flowed into the treated waste temporary storage receptacle until it is desired to replace the treated waste temporary storage receptacle with another identical treated waste temporary storage receptacle into which the mixture of liquid waste and liquid disinfectant thereafter flows.

50. A method as recited in claim 40 wherein the liquid waste is pumped by a liquid waste pump and the method further comprises the steps of:

monitoring whether liquid waste is present in the suction chamber at a level above a threshold pumping level; and disabling operation of the liquid waste pump when the level of the liquid waste in the suction chamber is below the threshold pumping level.

51. A method as recited in claim 40 wherein the liquid waste and liquid disinfectant are mixed in a mixer and tubing through which the liquid waste and liquid disinfectant flow and the mixer are components of an integral disposable tube set, and the method further comprises the step of:

installing a new disposable tube set before treating biohazardous liquid waste collected from any particular patient.

52. In a biohazardous liquid waste collection and treatment system including:

a suction chamber including an internal liquid waste receptacle and a liquid waste intake port;

a suction tube connected to the liquid waste intake port on the suction chamber;

a vacuum source connected to the suction chamber that creates a vacuum in the suction chamber to draw liquid waste through the suction tube into the internal liquid waste receptacle in the suction chamber;

a liquid disinfectant reservoir;

a liquid waste pump;

a liquid disinfectant pump;

a treated waste temporary storage receptacle that receives a mixture of liquid waste and liquid disinfectant from the waste treatment mixer; and an integral disposable tube set for use in the system, the disposable tube set comprising:

a main tube;

an untreated liquid waste tube leading into the main tube for flowing untreated liquid waste from the internal waste receptacle of the suction chamber to the main tube, the untreated liquid waste tube having a quick connect inlet;

a liquid disinfectant tube leading into the main tube for flowing liquid disinfectant from the liquid disinfectant reservoir to the main tube, the liquid disinfectant tube having a quick connect inlet; and a motionless mixer installed within the main tube.

53. An integral disposable tube set as recited in claim 52 further comprising:
 a pressure tap tube installed between the quick connect inlet for the untreated liquid waste tube and the motionless mixer.

54. An integral disposable tube set as recited in claim 52 wherein the recited untreated liquid waste tube is a first untreated liquid waste tube and the tube set further comprises one or more additional untreated liquid waste tubes each leading into the main tube at a location upstream of the location in which the liquid disinfectant tube leads into the main tube, each additional untreated liquid waste tube having a quick connect inlet.

55. An integral disposable tube set as recited in claim 52 wherein the tube set is constructed of a resilient material and the size of the liquid disinfectant tube is chosen in proportion to the size of the main tube to accurately meter the amount of liquid disinfectant pumped through the liquid disinfectant tube in proportion to the amount of untreated liquid waste pumped through the main tube.

* * * * *